(12) United States Patent
Nagae et al.

(10) Patent No.: US 9,572,498 B2
(45) Date of Patent: Feb. 21, 2017

(54) ULTRASONIC PROBE AND INSPECTION APPARATUS EQUIPPED WITH THE ULTRASONIC PROBE

(71) Applicant: CANON KABUSHIKI KAISHA, Tokyo (JP)

(72) Inventors: Kenichi Nagae, Kawasaki (JP); Yasufumi Asao, Atsugi (JP); Kazuhiko Fukutani, Yokohama (JP); Katsumi Nakagawa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 75 days.

(21) Appl. No.: 13/804,889

(22) Filed: Mar. 14, 2013

(65) Prior Publication Data

US 2013/0197345 A1 Aug. 1, 2013

Related U.S. Application Data

(62) Division of application No. 12/145,224, filed on Jun. 24, 2008, now abandoned.

(30) Foreign Application Priority Data

Jun. 29, 2007 (JP) .................. 2007-172746
Jun. 4, 2008 (JP) .................. 2008-146997

(51) Int. Cl.
*A61B 8/14* (2006.01)
*A61B 5/00* (2006.01)
*G01N 29/24* (2006.01)

(52) U.S. Cl.
CPC .......... *A61B 5/0095* (2013.01); *A61B 5/0059* (2013.01); *A61B 5/72* (2013.01); *A61B 5/742* (2013.01);
(Continued)

(58) Field of Classification Search
USPC .................. 600/407, 437, 459, 476, 479
See application file for complete search history.

(56) References Cited

U.S. PATENT DOCUMENTS 3,995,934 A 12/1976 Nath ............................ 350/96
4,385,634 A 5/1983 Bowen ....................... 128/653
(Continued)

FOREIGN PATENT DOCUMENTS

| JP | 7-181489 | 7/1995 |
| JP | 9-145683 | 6/1997 |

(Continued)

OTHER PUBLICATIONS

Japanese Office Action issued Jul. 23, 2013 in counterpart application No. 2008-146997, with translation.

(Continued)

*Primary Examiner* — Joel F Brutus
(74) *Attorney, Agent, or Firm* — Fitzpatrick, Cella, Harper & Scinto (57) ABSTRACT

An ultrasonic probe includes a light irradiating portion configured to radiate light for generating ultrasonic waves from a light absorber, an ultrasonic transducing portion configured to transduce the ultrasonic waves to an electric signal, and a light guide member configured to introduce light from a light source to the light irradiating portion. A light irradiating region of the light irradiating portion is included within an ultrasonic receiving region of the ultrasonic transducing portion.

28 Claims, 8 Drawing Sheets

(52) U.S. Cl.
CPC . *G01N 29/2418* (2013.01); *G01N 2291/02475* (2013.01)

(56) References Cited

U.S. PATENT DOCUMENTS

| | | | |
|---|---|---|---|
| 4,900,145 A | 2/1990 | Akiyama | 351/221 |
| 5,228,109 A * | 7/1993 | Fujii et al. | 392/419 |
| 5,467,779 A | 11/1995 | Smith et al. | 128/660.1 |
| 5,619,476 A | 4/1997 | Haller et al. | 367/181 |
| 5,713,356 A | 2/1998 | Kruger | 128/653.1 |
| 6,264,610 B1 | 7/2001 | Zhu | 600/443 |
| 6,773,126 B1 | 8/2004 | Hatjasalo et al. | 362/31 |
| 6,967,698 B2 | 11/2005 | Tanoue et al. | 349/62 |
| 7,639,916 B2 | 12/2009 | Fine | 385/131 |
| 2004/0236223 A1 | 11/2004 | Barnes et al. | 600/459 |
| 2005/0004458 A1 | 1/2005 | Kanayama et al. | 600/437 |
| 2005/0187471 A1 | 8/2005 | Kanayama et al. | 600/437 |
| 2006/0184049 A1 | 8/2006 | Tsujita | 600/478 |
| 2007/0167814 A1* | 7/2007 | Wakabayashi | A61B 8/12 600/459 |

FOREIGN PATENT DOCUMENTS

| | | |
|---|---|---|
| JP | 2003-290126 | 10/2003 |
| JP | 2004-147940 | 5/2004 |
| JP | 2004-351023 | 12/2004 |
| JP | 2005-024855 | 1/2005 |
| JP | 2005-218684 | 8/2005 |

OTHER PUBLICATIONS

Japanese Office Action issued Nov. 13, 2012 in counterpart application No. 2008-146997.

\* cited by examiner

ULTRASONIC PROBE AND INSPECTION APPARATUS EQUIPPED WITH THE ULTRASONIC PROBE

This application is a division of prior U.S. patent application Ser. No. 12/145,224 filed Jun. 24, 2008, now abandoned, the contents of which are incorporated by reference herein, as if set forth in full.

BACKGROUND OF THE INVENTION

Field of the Invention

The present invention relates to an ultrasonic probe suitable for use in an inspection utilizing a photoacoustic effect, and also relates to an inspection apparatus equipped with the ultrasonic probe.

Description of the Related Art

An inspection apparatus capable of obtaining a tomographic image or a three-dimensional image of a sample by utilizing a photoacoustic effect is proposed, for example, as described in U.S. Pat. No. 4,385,634. Such a technique is generally known as PhotoAcoustic Tomography and is called a "PAT technique".

A process of taking an image by the PAT technique is performed as follows:
1) Light is irradiated to a sample from the exterior.
2) The light propagates inside the sample.
3) The light is absorbed by a portion inside the sample where a light absorption coefficient is large.
4) The portion inside the sample is heated by the light absorption.
5) The heated portion expands.
6) Ultrasonic waves are generated upon the expansion.
7) The ultrasonic waves propagate inside the sample.
8) The propagating ultrasonic waves are received by an ultrasonic probe.
9) A tomographic image or a three-dimensional image of the sample is reconstructed by analyzing, e.g., time differences between the arrived ultrasonic waves.

Thus, the PAT technique has been so far studied primarily by research institutes in view of advantages resulting from the fact that the technique is based on comparatively simple processing, and that components such as a light source and an ultrasonic probe, which are already used for other purposes, can be employed as they are. In particular, an application to a biological information inspection apparatus for obtaining a high-resolution tomographic image is expected.

However, the PAT technique has the problem that, despite a demand for irradiating light to an inspection target from a position as close as possible to the target, the ultrasonic probe serving as a receiving unit impedes satisfaction of the demand by itself.

Figure 11:
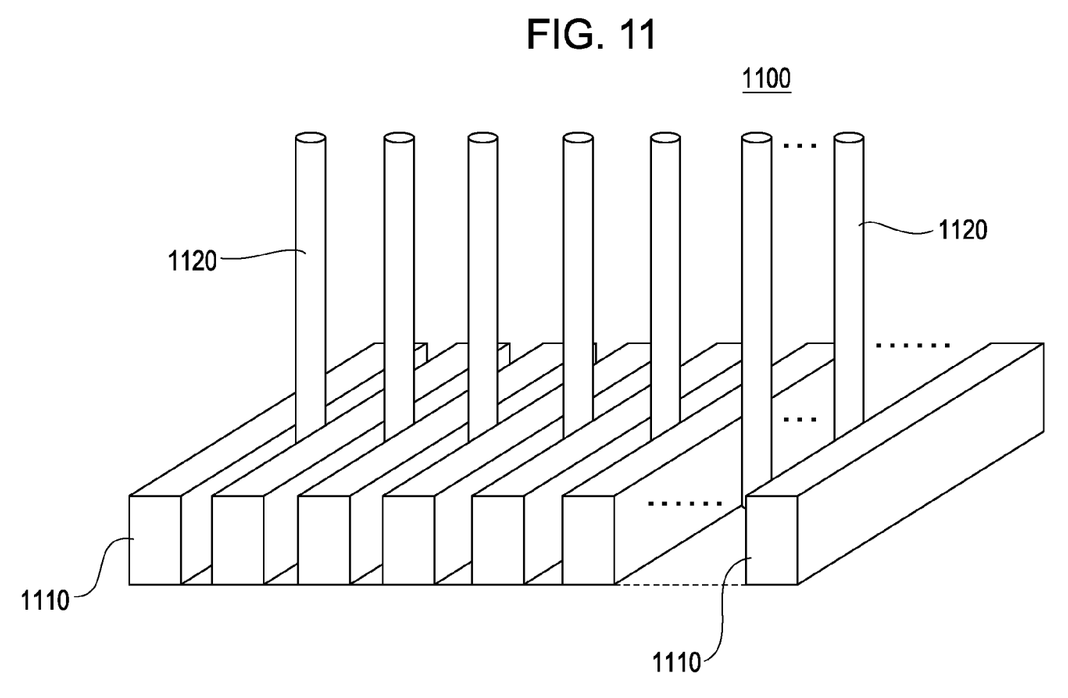
FIG. 11 is a schematic view illustrating the related art.

To overcome this problem, U.S. Patent Application Publication No. 2005/0004458 proposes an ultrasonic probe 1100 shown in FIG. 11.

In FIG. 11, ultrasonic transducing units (ultrasonic transducers) 1110 are arrayed at a predetermined interval. Optical fibers (light irradiating units) 1120 are disposed in gaps between the ultrasonic transducers 1110 adjacent to each other, and a predetermined light is radiated toward an inspection target from the optical fibers 1120. Ultrasonic waves generated upon absorption of the light by tissues (i.e., light absorbers) inside the inspection target are transduced to an electric signal by the ultrasonic transducers 1110.

Because the ultrasonic probe 1100 proposed in U.S. Patent Application Publication No. 2005/0004458 includes light irradiating regions each formed between ultrasonic receiving regions, an effect of the shade of the ultrasonic probe 1100 can be reduced in comparison with the case of irradiating the light from a position around the ultrasonic probe 1100.

Even with the ultrasonic probe proposed in U.S. Patent Application Publication No. 2005/0004458, however, since the ultrasonic receiving regions and the light irradiating regions are disposed at different positions, a further improvement of sensitivity is demanded, for example, when observing capillary vessels that are positioned in the shallowest portion under the skin of a living body. Also, when the ultrasonic probe having the structure of FIG. 11 is used with a capacitive micromachined ultrasonic transducer (CMUT) using a silicon substrate, which is described in U.S. Pat. No. 5,619,476, it is difficult to fabricate the ultrasonic probe due to the necessity of boring a through hole in the silicon substrate.

SUMMARY OF THE INVENTION

The present invention provides a novel ultrasonic probe which is optimum for taking an image of the internal structure of an inspection target by utilizing a photoacoustic effect, and also provides an inspection apparatus employing the ultrasonic probe.

The ultrasonic probe includes a light irradiating portion configured to radiate light for generating ultrasonic waves from a light absorber, an ultrasonic transducing portion configured to transduce the ultrasonic waves to an electric signal, and a light guide member configured to introduce the light from a light source to the light irradiating portion. A light irradiating region of the light irradiating portion is included within an ultrasonic receiving region of the ultrasonic transducing portion.

According to the present invention, a novel ultrasonic probe can be obtained which is optimum for taking an image of the internal structure of an inspection target by utilizing a photoacoustic effect, and an inspection apparatus employing the ultrasonic probe can also be obtained.

Further features of the present invention will become apparent from the following description of exemplary embodiments with reference to the attached drawings.

DESCRIPTION OF THE EMBODIMENTS

Figure 10A:
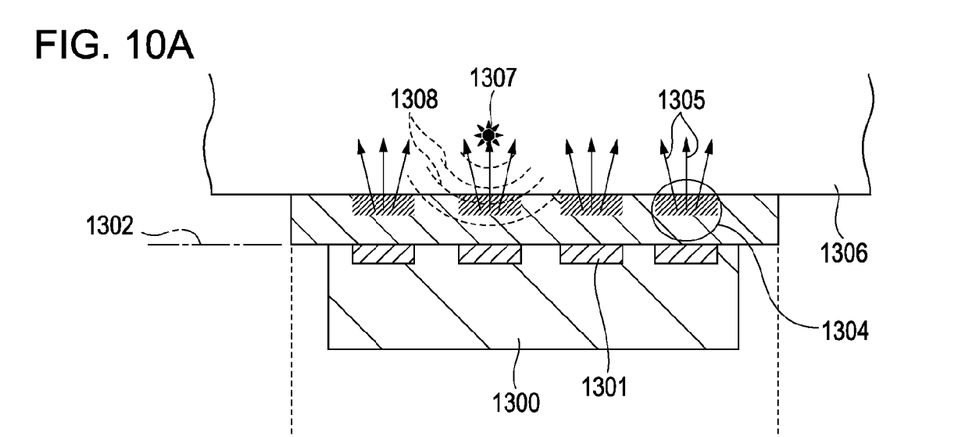
FIGS. 10A and 10B are schematic views illustrating the basic concept of the ultrasonic probe according to exemplary embodiments of the present invention.
Figure 10B:
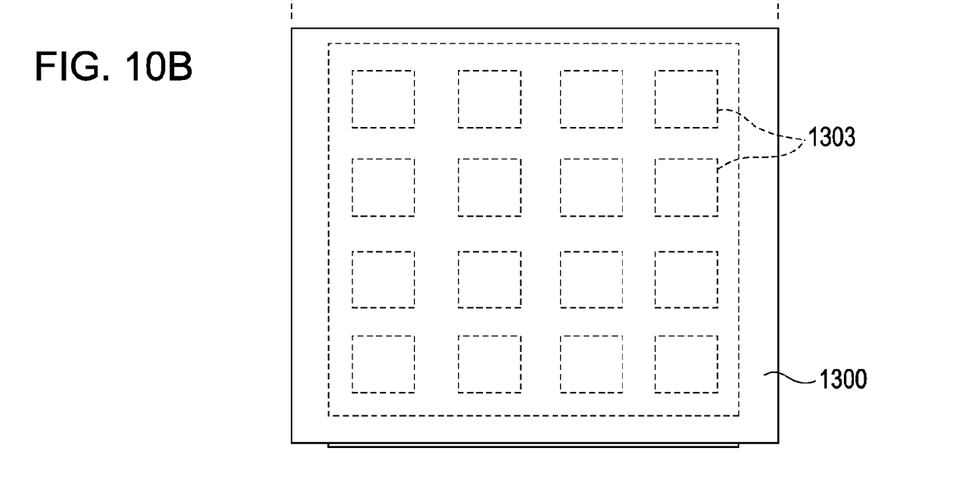

The basic concept of the ultrasonic probe according to exemplary embodiments of the present invention will be described with reference to FIGS. 10A and 10B. FIG. 10A is a sectional view, and FIG. 10B is a plan view as viewed from the incident side of ultrasonic waves. In FIGS. 10A and 10B, numeral 1300 denotes an ultrasonic probe, and 1301 denotes each of individual ultrasonic transducing portions. The ultrasonic transducing portions 1301 share an ultrasonic receiving surface 1302.

In the ultrasonic receiving surface 1302, the ultrasonic transducing portions 1301 have respective ultrasonic receiving regions 1303 with reception sensitivity. Numeral 1304 denotes each of individual light irradiating portions. The light irradiating portions 1304 are arranged in front of the ultrasonic receiving surface 1302 and have light irradiating regions from which light is irradiated toward an inspection target 1306.

The light irradiating portions 1304 can be arranged over the entire ultrasonic receiving surface 1302 on condition that the ultrasonic receiving regions 1303 include the light irradiating portions 1304. In other words, it is just required that the light irradiating regions are included within the ultrasonic receiving regions 1303. From the viewpoint of light utilization efficiency, however, the ultrasonic receiving regions 1303 and the light irradiating regions are preferably arranged to face each other, as shown in FIG. 10A. More preferably, the center of each of the ultrasonic receiving regions 1303 matches the center of each of the light irradiating regions.

If there is a light absorber 1307 in an inspection target 1306, light 1305 radiated from the light irradiating portions 1304 toward the inspection target 1306 is absorbed by the light absorber 1307 so that the light absorber 1307 is heated and radiates strong photoacoustic waves 1308 which are received by the ultrasonic transducing portions 1301.

Since the light is radiated from an area positioned just in front of the ultrasonic receiving regions 1303, the photoacoustic waves 1308 can be detected with a high sensitivity even when the light absorber 1307 is present very close to the surface of the inspection target 1306. Also, since the light irradiating portions 1304 are positioned in front of the ultrasonic receiving surface 1302, there is no need of boring a substrate which is used to form the ultrasonic probe 1300. Therefore, even the ultrasonic probe formed on a silicon substrate, such as a CMUT, can be easily manufactured.

First Exemplary Embodiment

An ultrasonic probe according to a first exemplary embodiment of the present invention will be described with reference to FIG. 1.

Figure 1:
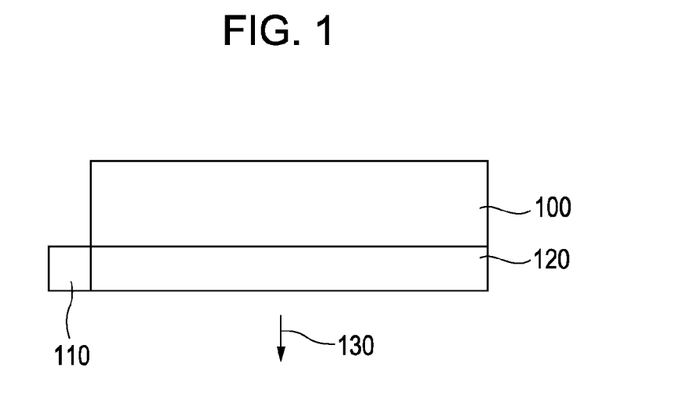
FIG. 1 is a schematic view illustrating an ultrasonic probe according to a first exemplary embodiment of the present invention.

In FIG. 1, numeral 100 denotes an ultrasonic probe, 110 denotes a light source, 120 denotes a diffusion plate for diffusing light, and 130 denotes an irradiated light.

More specifically, as shown in FIG. 1, the diffusion plate 120 for diffusing light is disposed on the ultrasonic receiving surface side, and the light is radiated through the diffusion plate 120 in a direction opposed to the direction in which ultrasonic transducing portions receive ultrasonic waves.

The present invention is intended to minimize a physical distance between an inspection target, e.g., a living body, and a light source and a physical distance between the inspection target and the ultrasonic probe, thus reducing attenuations of both the light radiated from the light source and the ultrasonic waves generated from the inside of the living body, which are caused by the living body.

One practical method for realizing the structure of FIG. 1 can be a liquid-crystal backlight of the so-called edge light type.

The edge light type backlight refers to a backlight technique that is generally practiced in medium- or small-sized liquid crystal displays for cell phones and notebook PCs by employing a surface illuminant which comprises a light source, a light guide member, and a diffusion plate.

Figure 2:
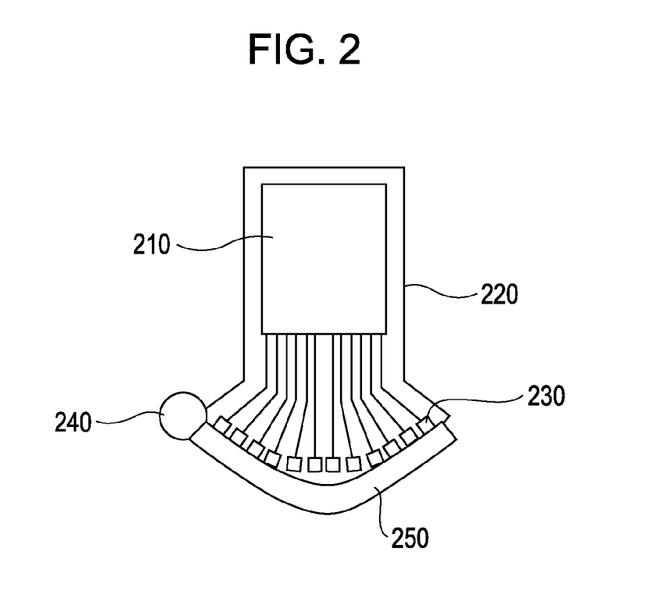
FIG. 2 is another schematic view illustrating the ultrasonic probe according to the first exemplary embodiment of the present invention.

Referring to FIG. 2, numeral 210 denotes a circuit board including a switch circuit for selecting ultrasonic vibrators to be driven, numeral 220 denotes an ultrasonic probe, and 230 denotes a plurality of ultrasonic vibrators included in the ultrasonic probe. Further, numeral 240 denotes a light source, and 250 denotes a light guide member. With such a structure, the light can be irradiated to the inspection target positioned just under the ultrasonic probe.

The light source 240 (one or plural sources of light) is disposed at a side of the light guide member 250. The light propagates through the light guide member 250 while repeating total reflection. The light can be taken out to the exterior of the light guide member 250 by shaping a surface of the light guide member 250 or providing a scatterer in the surface of the light guide member 250 so as not to satisfy the condition of total reflection. As a result, the surface illuminant is obtained.

By controlling the surface shape or the scatterer, the surface illuminant can be designed to minimize variations in an in-plane luminance distribution. However, it is often difficult to sufficiently reduce in-plane variations in quantity of the radiated light by using only the light guide member 250.

For that reason, the diffusion plate or the like is employed to average the in-plane distribution of quantity of the radiated light, thus providing a surface illuminant that has a uniform light quantity.

A diffusion plate used in the liquid crystal display mainly serves to provide an image with uniform brightness in a display surface, and to reduce a significant change of luminance when the display surface is observed from various angles.

In contrast, the diffusion plate used in the ultrasonic probe according to the first exemplary embodiment mainly serves to irradiate the light in a maximum quantity while reducing a surface density of the light. A light density per unit area allowable for irradiation to a living body is determined according to industrial standards, and the irradiation of light at a density exceeding the allowable level is inhibited.

Accordingly, a larger quantity of light has to be irradiated in order to maximize the photoacoustic effect. To that end, variations in the in-plane distribution of light density should be held at a minimum. Therefore, the diffusion plate is used in the ultrasonic probe according to the first exemplary embodiment.

Further, from the viewpoint of efficiently irradiating the light to the inspection target, such as a tumor in a living body, it is desired that the light from the light source reaches the inspection target through the shortest distance. In other words, the ultrasonic probe is preferably designed so as to increase the quantity of light propagating in the direction normal to the surface light source.

The light source used in the present invention is selected to have a wavelength in an near-infrared range, as required, taking into account that the light source preferably has a wavelength at which an absorption by the inspection target appears significantly, and that the wavelength of the light source is preferably in a range where the light is highly transmissive through other areas in the living body than the target. In consideration of monochromaticity as well, a near-infrared laser is used.

Regarding the light guide member, a thin light guide member has recently been developed with an intent to realize a flexible structure of LCD, and it can be used as appropriate. The related art is disclosed, for example, in U.S. Pat. No. 6,773,126. Such a light guide member can be formed directly on the ultrasonic probe by an imprinting process, for example.

As with the need of increasing efficiency in the LCD backlight, the present invention also requires a larger quantity of light to be irradiated to the living body. The technique described, for example, in U.S. Pat. No. 6,967,698 can be employed to increase the quantity of light emitting from the light guide member.

Even when a light guide member is used, a light reflection layer can be disposed in the light guide member so that a larger quantity of light is irradiated to the living body.

The light reflection layer can be a metallic reflection plate that is ordinarily used. Because the living body is irradiated in the present invention with light of various wavelengths, including visible light and infrared light, the reflection plate is formed by using a metal that has a high reflectivity in the required wavelength band.

In that case, the reflectivity of the light reflection plate is set to be 90% or more from the viewpoint of increasing the efficiency.

If the reflectivity of the light reflection layer or the luminous efficiency of an illuminant is small, heat is generated in a light emission area, thus causing an error in measurement. To prevent such a measurement error, it is advantageous that the ultrasonic probe used in practice has a higher heat radiation effect.

Assuming that the wavelength of the ultrasonic wave detected by the ultrasonic transducing portion is $\lambda$, the thickness of the light guide member is set to $(0.25 \times \lambda)$. The acoustic impedance of a material forming the light guide member is set at least to a value between the acoustic impedance of the ultrasonic transducing portion and the acoustic impedance of the inspection target. For example, the acoustic impedance of the light guide member can be set to a geometrical mean value of the acoustic impedance of the ultrasonic transducing portion and the acoustic impedance of the inspection target.

The ultrasonic transducing portions can be formed by using a piezoelectric substance, such as PZT, or a semiconductor. Also, the ultrasonic transducing portions can be constituted in the form separated into a plurality of transducers or as an array of ultrasonic vibrators. An ultrasonic receiving unit employed in the present invention is not particularly limited and can be a unit utilizing, e.g., a magnetostrictive phenomenon, an electrostrictive effect, a change of electrostatic attraction and capacity, or light.

The ultrasonic probe according to the first exemplary embodiment can be further used to transmit and receive ultrasonic waves and to provide an image by processing the reflected ultrasonic waves. The image provided by processing the reflected ultrasonic waves and the image obtained based on the photoacoustic effect can be displayed in an overlapping relation. Alternatively, the image provided by processing the reflected ultrasonic waves and the image obtained based on the photoacoustic effect can be displayed side by side.

In addition, the ultrasonic probe according to the first exemplary embodiment can include a photo detector. The photo detector can be used as a light-receiving portion for not only measurement and calibration of quantity and distribution of the incident (irradiated) light, but also for DOT (Diffuse Optical Tomography) which visualizes the interior of an observation target by causing light to transmit in the observation target.

Second Exemplary Embodiment

Figure 3:
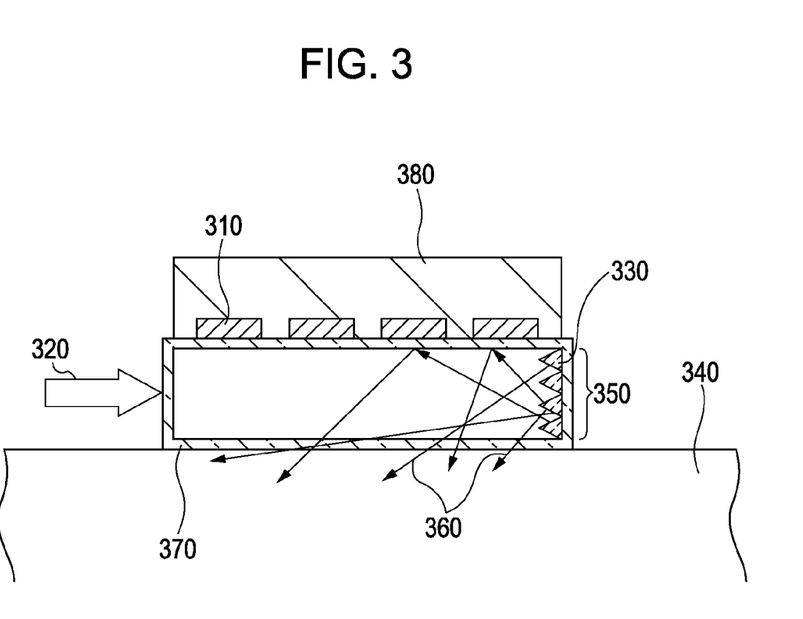
FIG. 3 is a schematic view illustrating an ultrasonic probe according to a second exemplary embodiment of the present invention.

An ultrasonic probe according to a second exemplary embodiment of the present invention will be described with reference to FIG. 3. FIG. 3 is a schematic sectional view illustrating the ultrasonic probe according to the second exemplary embodiment.

In FIG. 3, the ultrasonic probe comprises an ultrasonic transducing portion 310, such as a piezoelectric transducer or a CMUT, an input light (laser) 320 introduced from a light source, a scatterer 330, an inspection target 340, an end surface 350 of a light guide member 370, a laser beam 360, the light guide member 370, and a substrate 380 of the ultrasonic probe.

On one side of the substrate 380 of the ultrasonic probe, the ultrasonic transducing portions 310 are arranged in a two-dimensional array. For example, the substrate 380 has a 3-cm square shape, and each of the ultrasonic transducing portions 310 has a 0.5-mm square shape. Those ultrasonic transducing portions 310 are arranged at a pitch of 2 mm in each of the lengthwise and widthwise directions. When the ultrasonic transducing portion 310 is a CMUT, the frequency changes depending on the size of the ultrasonic transducing portion. Therefore, a plurality of small ultrasonic transducing portions having respective desired bands can be arranged side by side and can be driven by interconnecting their electrodes as required.

The light guide member 370 is disposed on a surface of the substrate 380 on the side including the ultrasonic transducing portions 310. The laser beam 320 is irradiated from one end of the light guide member 370 to propagate through the light guide member 370.

After propagating through the light guide member 370, the laser beam 320 is scattered by the light scatterer 330 disposed at the end surface 350 and is introduced into the inspection target 340. The light scatterer 330 can be arranged on three of four surfaces of the light guide member 370, which are vertically disposed relative to a horizontal incident axis of the laser beam 320, except for the remaining one surface upon which the laser beam 320 is incident. Such an arrangement enables the laser beam to be introduced into the inspection target 340 with higher efficiency. The light guide member 370 is formed of a hollow housing made of, e.g., vinyl or glass, and is filled with a liquid, e.g., water.

In particular, portions of the light guide member 370, which contact the inspection target 340 and the ultrasonic transducing portions 310, can be formed, for example, of a Mylar film that is highly transmissive to ultrasonic waves. The light guide member using the Mylar film can introduce the ultrasonic waves generated from the inspection target 340 into the ultrasonic transducing portions 310 with higher efficiency than the light guide member made of a solid material. Further, the light scatterer 330 can be formed in any shape so long as it has asperities (unevenness) in larger size than the wavelength used.

Third Exemplary Embodiment

Figure 4A:
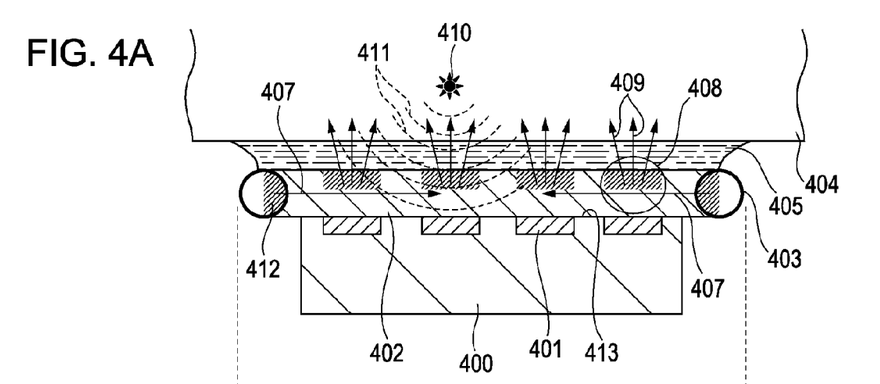
FIGS. 4A and 4B are schematic views illustrating an ultrasonic probe according to a third exemplary embodiment of the present invention.
Figure 4B:
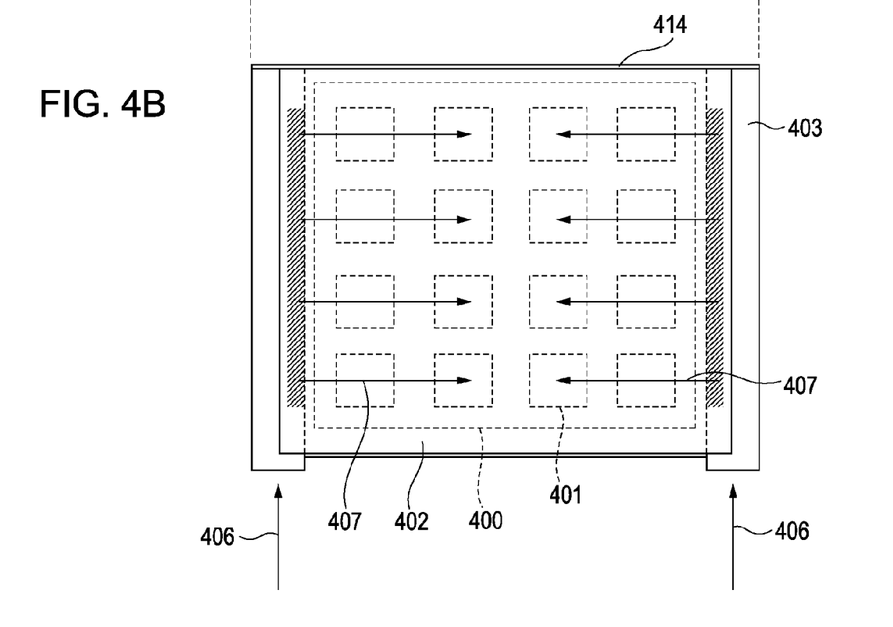

An ultrasonic probe according to a third exemplary embodiment of the present invention will be described below with reference to FIGS. 4A and 4B. FIG. 4A is a sectional view of the ultrasonic probe according to the third exemplary embodiment, and FIG. 4B is a plan view.

On one side of a substrate 400 of the ultrasonic probe, ultrasonic transducing portions 401, such as piezoelectric transducers or CMUTs, are arranged in a two-dimensional array.

A light guide member 402 is disposed on a surface of the substrate 400 on the side including the ultrasonic transducing portions 401. Terminal ends 403 of optical fibers are fixed to opposite ends of the light guide member 402. The light guide member 402 contacts the inspection target 404 with an acoustic coupling member 405 interposed between them.

A light 406 having propagated through the optical fibers 403 is introduced into the light guide member 402 from the opposite ends thereof. The light 406 introduced into the light guide member 402 propagates through the interior of the light guide member 402 as indicated by arrows 407, and is then radiated toward the inspection target 404 from light irradiating portions 408 as indicated by arrows 409. If there is a light absorber 410 inside the inspection target 404, the temperature of the light absorber 410 increases selectively to such an extent that the light absorber 410 emits photoacoustic waves 411. The photoacoustic waves 411 are received by the ultrasonic transducing portions 401 through the acoustic coupling member 405.

To promote the introduction of the light 406 into the light guide member 402 from the optical fibers 403, a textured structure is provided in a lateral surface 412 of each optical fiber 403, or fine particles having a light diffusion function are dispersed in the optical fiber.

In a desired state, the light 406 is uniformly introduced into the light guide member 402 over the entire opposite ends thereof. The reason is that, if the light is non-uniformly introduced, variations are caused in the irradiated light intensity in the lengthwise direction of the substrate. To eliminate such variations, the size of the textured structure provided in the optical-fiber lateral surface 412 and/or the density of fine particles dispersed in the optical fibers are adjusted so as to gradually increase the degree of dispersion (i.e., a light diffusion function) from the entry side of the light 406 toward the innermost side. It is also desired that the light radiation 409 from the light guide member 402 is uniformly performed over the entire substrate.

In particular, when observing the light absorber 410 which is located at a shallow position from the surface of the inspection target 404, it is more efficient to selectively introduce the light 406 through the light irradiating portions 408 which are positioned just above the ultrasonic transducing portions 410. To that end, the refractive index of the light guide member 402 is set to be larger than that of the acoustic coupling member 405 so that the propagating light 407 is enclosed within the light guide member 402 by total reflection.

Further, light diffusion in the light irradiating portions 408 can be promoted by selectively providing a textured structure in the surface of the light guide member 402, or by dispersing fine particles with a light diffusion function inside the light guide member 402. Additionally, it is desired that the light diffusion function is gradually enhanced from the entry side of the propagating light 407 toward the innermost side.

On the other hand, the light guide member 402 is required to efficiently propagate the photoacoustic waves 411 from the light absorber 410 in the direction of thickness of the light guide member 402. To that end, the light guide member 402 is made of a material having an acoustic impedance between those of the inspection target 404 and the ultrasonic transducing portions 401. Further, the material of the light guide member 402 is selected to have a large Poisson's ratio (near 0.5) in order not to impede vibrations in the ultrasonic transducing portions. As a material satisfying the above-described requirements, there is silicone rubber conventionally used for an acoustic lens in a one-dimensional ultrasonic probe.

Because the refractive index of silicone rubber with respect to visible light or near-infrared light is about 1.4-1.5, water (refractive index of 1.33) or ethanol (refractive index of 1.37), for example, can be used as the acoustic coupling member 405 from the viewpoint of enclosing light within the light guide member 402.

When the textured structure is formed in the surface of the silicone rubber, the size of the textured structure is required to be not smaller than the wavelength (0.5-1.5 µm) of the used light from the viewpoint of light diffusion. However, if the size of the textured structure is near the wavelength (1.5-0.15 mm at frequency of 1-10 MHz) of ultrasonic waves, the textured structure scatters the ultrasonic waves. Therefore, the size of the textured structure is set to a value between the wavelength of the used light and the wavelength of the ultrasonic waves.

The dispersed fine particles can be made of $SiO_2$ having a particle size of about 2 µm, for example.

In addition, providing a light reflection surface 413 between the light guide member 402 and the substrate 400 and between the light guide member 402 and the ultrasonic transducing portions 401 is effective in not only increasing the light utilization efficiency, but also preventing undesired acoustic waves (noise) from being generated in the substrate surface, etc. Further, when the light guide member 402 has an end through which the light is not introduced, the provision of a light reflection layer 414 enables the light to be utilized with higher efficiency.

Fourth Exemplary Embodiment

An ultrasonic probe according to a fourth exemplary embodiment of the present invention will be described with reference to FIG. 5. A description of components in common to those in the third exemplary embodiment is omitted here.

In the fourth exemplary embodiment, the light irradiating portions 408 are constituted by forming the surface of the light guide member 402 to have curved surface portions. In the curved surface portions, the condition of total reflection based on the difference in refractive index between the light guide member 402 and the acoustic coupling member 405 is not satisfied optically, and the light is radiated toward the inspection target 404 through the curved surface portions.

Figure 5:
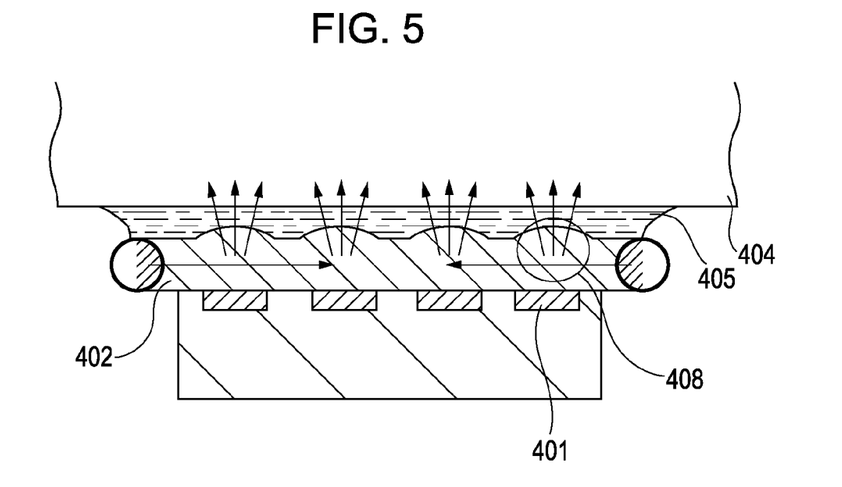
FIG. 5 is a schematic view illustrating an ultrasonic probe according to a fourth exemplary embodiment of the present invention.

In an acoustic point of view, because the velocity of sound in silicone rubber is 900-1000 m/sec and the velocity of sound in water is 1480 m/sec, the curved surface portions which are upwardly convex as shown in FIG. 5 act as convex lenses with respect to acoustic waves. Therefore, even when each of the ultrasonic transducing portions 401 have a size fairly smaller than an interval between two ultrasonic transducing portions adjacent to each other in the array thereof, energy of the photoacoustic waves can be efficiently taken into the ultrasonic transducing portions 401. Increasing the interval between the individual ultrasonic transducing portions 401 is also effective in preventing interference between the individual ultrasonic transducing portions and improving quality of an image.

Fifth Exemplary Embodiment

Figure 6:
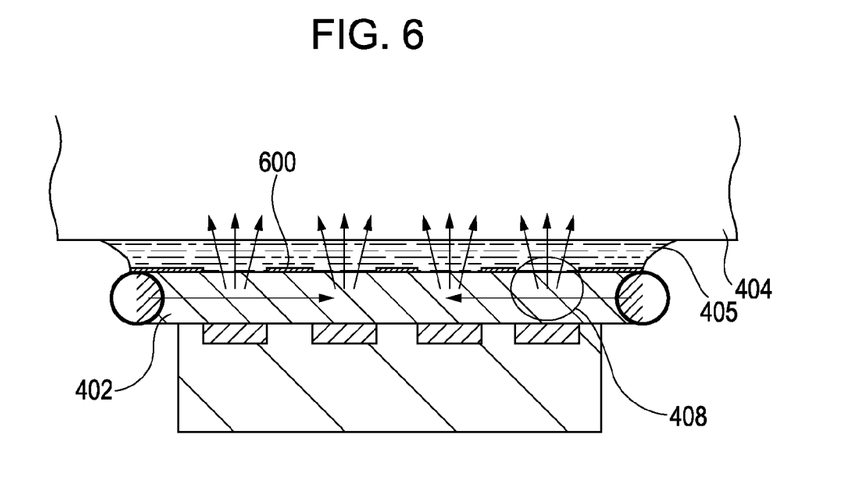
FIG. 6 is a schematic view illustrating an ultrasonic probe according to a fifth exemplary embodiment of the present invention.

An ultrasonic probe according to a fifth exemplary embodiment of the present invention will be described with reference to FIG. 6. A description of components in common to those in the third and fourth exemplary embodiments is omitted here.

In the fifth exemplary embodiment, the refractive index of the light guide member 402 is set to be smaller than that of the acoustic coupling member 405. Therefore, the condition for enclosing the light is not satisfied and the light is radiated toward the inspection target 404.

However, the light can be efficiently utilized by forming, on the surface of the light guide member 402, a light-shield mask layer 600 which has openings in positions corresponding to the light irradiating portions 408. In other words, areas (openings) not covered with the light-shield mask layer 600 serve as the light irradiating portions.

As with the third exemplary embodiment described above with reference to FIGS. 4A and 4B, the light can be irradiated with uniform intensity by setting the opening size such that the openings positioned nearer to the input side of the propagating light 407 have smaller sizes and the openings positioned nearer to the innermost side have larger sizes.

In the fifth exemplary embodiment, the acoustic coupling member 405 can be generally made of a material having a high viscosity. For example, even when glycerin (refractive index of 1.47) is used as the material of the acoustic coupling member 405, the setting not to satisfy the light enclosing condition can be realized by selecting an appropriate type of silicone rubber of which refractive index is lower than that of glycerin. The highly-viscous acoustic coupling member 405 is convenient in use because the acoustic coupling member 405 becomes less apt to leak externally when it is inserted between the inspection target 404 and the light guide member 402.

Sixth Exemplary Embodiment

A sixth exemplary embodiment of the present invention will be described with reference to FIG. 7.

The sixth exemplary embodiment is described in connection with the case where the present invention is applied to mamma diagnosis (i.e., mammography).

Figure 7:
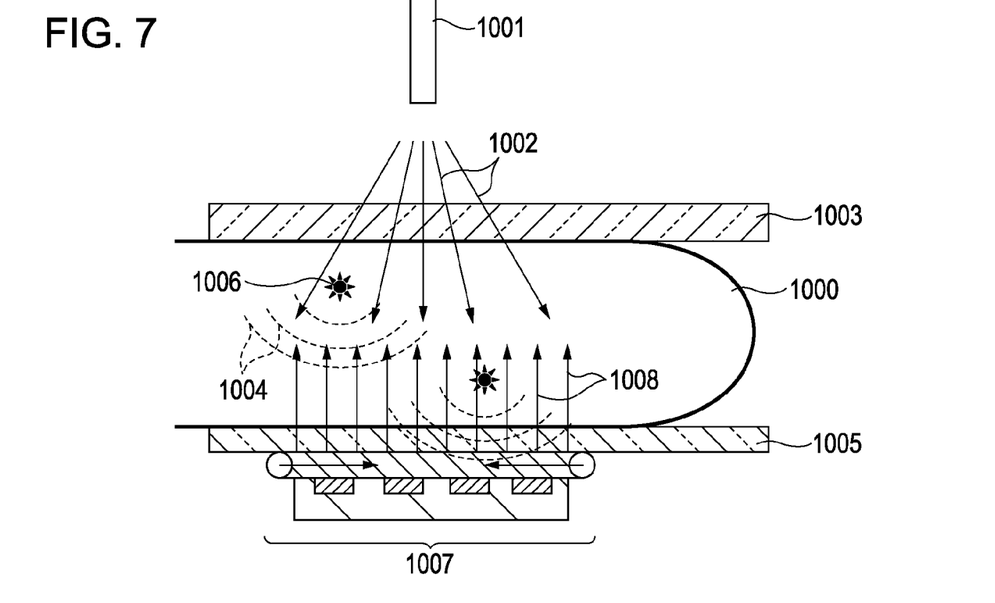
FIG. 7 is a schematic view illustrating an application example according to a sixth exemplary embodiment of the present invention.

In FIG. 7, a light source (optical fiber) 1001 is prepared as a radiation source of electromagnetic waves, and a light 1002 is irradiated to a mamma 1000. The mamma 1000 is sandwiched between a plate 1003 which is transparent to the light 1002 and a plate 1005 which is also transparent to the light 1002 and which allows ultrasonic waves 1004 to propagate well through it.

Further, numeral 1007 denotes an ultrasonic probe that is one of the ultrasonic probes described in the foregoing exemplary embodiments. With such an arrangement, as indicated by 1002 and 1008, since the light can be irradiated to the mamma 1000 from the both sides, an image of a tissue highly absorbing the light, e.g., a new blood vessel 1006 generated with a cancer, can be obtained at a high contrast. Further, since one of the ultrasonic probes described in the foregoing exemplary embodiments is used as the ultrasonic probe 1007, a portion which has been located in shades in the past can also be effectively illuminated by the light 1008 from the ultrasonic probe 1007.

Seventh Exemplary Embodiment

A seventh exemplary embodiment of the present invention will be described with reference to FIG. 8.

The seventh exemplary embodiment is also described in connection with the case where the present invention is applied to mamma diagnosis (i.e., mammography). The seventh exemplary embodiment uses two ultrasonic probes 1007, i.e., a first ultrasonic probe and a second ultrasonic probe, each being the same as that in the sixth embodiment.

The two ultrasonic probes 1007 can be constructed such that they have independent light sources and can generate light pulses at the same time under control by a common optical control unit. The arrangement may be modified such that a light pulse from a common light source is divided into two light pulses which are propagated to the ultrasonic probes through respective waveguides and are radiated from the light irradiating portions in each of the two ultrasonic probes.

Image data including lesser defects (artifacts) can be obtained by synthetically processing signals which are received by a plurality of ultrasonic probes at different incident angles, as in this seventh exemplary embodiment.

Figure 8:
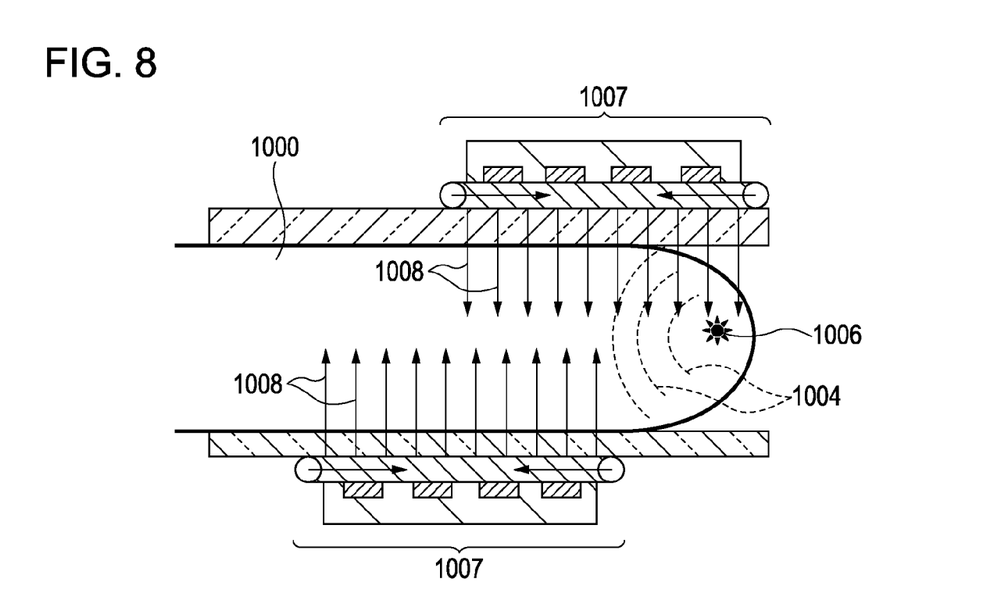
FIG. 8 is a schematic view illustrating another application example according to a seventh exemplary embodiment of the present invention.

The two ultrasonic probes can be arranged not only in an exactly opposed relation, but also in a state where they are opposed in a relatively shifted relation as shown in FIG. 8. In particular, when the new blood vessel 1006 is present at a position near the tip of the mamma 1000, photoacoustic waves generated from the new blood vessel 1006 can be effectively received by the lower ultrasonic probe 1007 having a larger contact surface with respect to the mamma if the new blood vessel 1006 can be illuminated with the light from the upper ultrasonic probe 1007 at a sufficient luminance.

Eighth Exemplary Embodiment

Inspection Apparatus

An inspection apparatus can be constructed by using one of the ultrasonic probes described in the foregoing exemplary embodiments. The inspection apparatus is practiced as an ultrasonic image forming apparatus utilizing the aforementioned PAT technique. Therefore, the inspection apparatus according to the eighth exemplary embodiment includes a display unit (monitor) for displaying, as image data, internal information of the inspection target by using received signals from the ultrasonic probe.

The internal information can be a tomographic image or a three-dimensional shape, for example, and it is provided by representing parameters regarding features of the inspection target in the form of an image.

Figure 9:
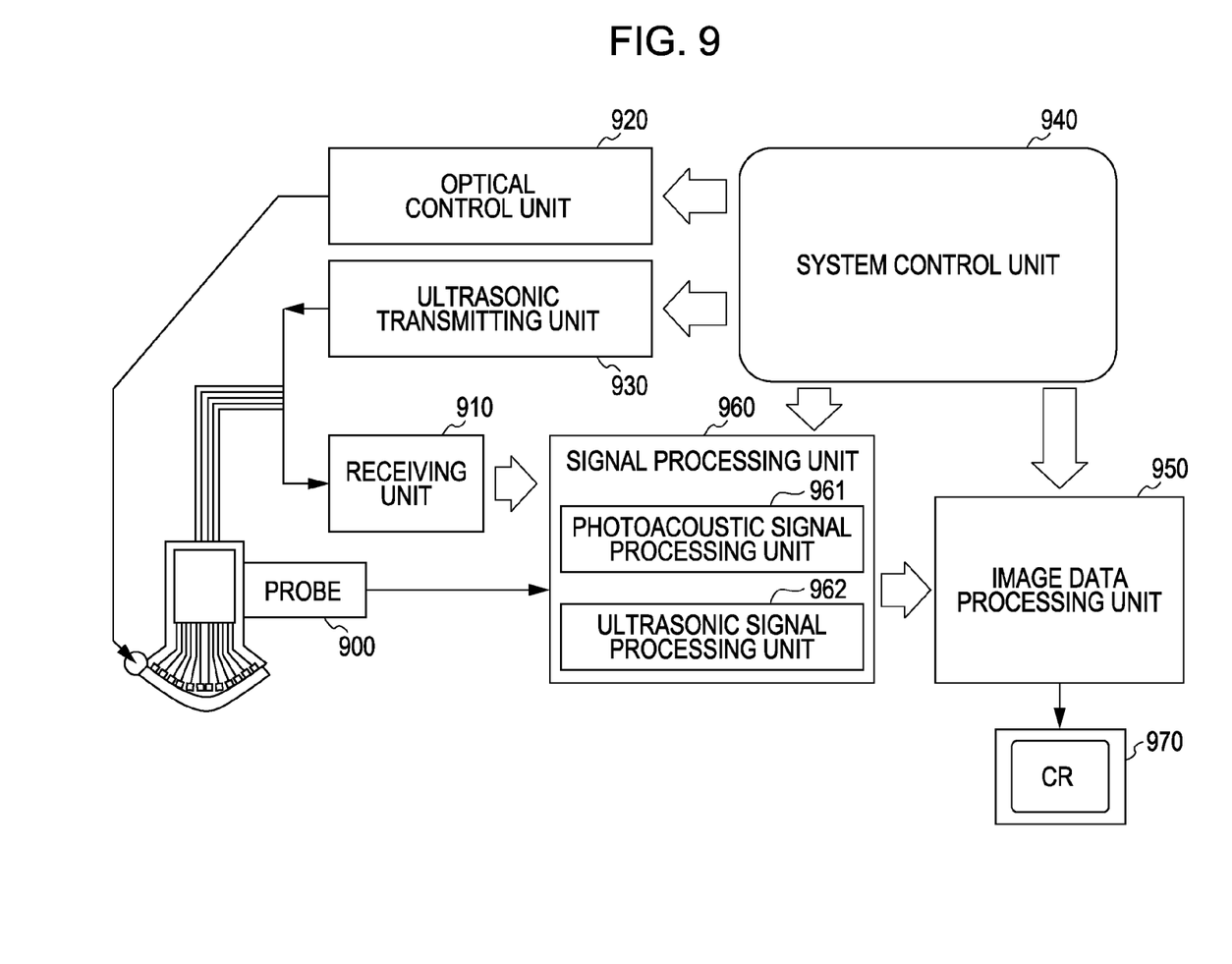
FIG. 9 is a schematic view illustrating an inspection apparatus according to an eighth exemplary embodiment of the present invention.

A practical example of the inspection apparatus is described below. FIG. 9 illustrates an inspection apparatus including an ultrasonic probe 900 which is the same as that described above with reference to FIG. 2, for example.

The inspection apparatus further includes an optical control unit 920 for controlling the wavelength, the driving timing, and the output of a light source, and an ultrasonic transmitting unit 930 for scanning ultrasonic waves to observe the interior of the inspection target. In the inspection apparatus employing the PAT technique, transmission of ultrasonic waves is not necessarily required. Signals output from a group of ultrasonic vibrators, which serve as the ultrasonic transducing portions, are transmitted in a wired or wireless way and are received by a receiving unit 910.

Numeral 960 denotes a signal processing unit including a photoacoustic signal processing unit 961 and an ultrasonic signal processing unit 962.

The photoacoustic signal processing unit 961 executes arithmetic and other processing of photoacoustic signals, which are obtained from the group of ultrasonic vibrators, to calculate the direction and the intensity of the photoacoustic signals generated in the inspection target.

When ultrasonic waves are transmitted, the ultrasonic signal processing unit 962 calculates the intensity of reflected ultrasonic waves depending on the transmitting direction of the ultrasonic waves. When no ultrasonic waves are transmitted, the ultrasonic signal processing unit 962 can be dispensed with.

An image data processing unit 950 executes, for example, reconstruction of an image, coordinate transformation, edge enhancement, contrast adjustment, and overlapping of an image obtained from the photoacoustic signals with an image obtained from the ultrasonic signals. Data processed by the image data processing unit 950 is displayed on the monitor 970.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2007-172746 filed Jun. 29, 2007 and of Japanese Patent Application No. 2008-146997 filed Jun. 4, 2008, which are hereby incorporated by reference herein in their entirety.

What is claimed is:

1. An ultrasonic probe comprising:
   a transducer array having a plurality of acoustic transducers each of which has a receiving surface so as to transduce an ultrasonic wave into an electrical signal;
   a light source; and
   a light diffusion member connected to said light source so as to diffuse light emitted from said light source into an inspection subject,
   wherein said light diffusion member has a propagating surface through which the ultrasonic wave is propagated from said light diffusion member to said transducer array,
   wherein said propagating surface is connected to said receiving surface,
   wherein said light diffusion member has a light irradiating surface located in opposition to said propagating surface, and
   wherein said light diffusion member extends along an extending direction from a first end to a second end, and wherein said light source is located next to one of said first end and said second end of said light diffusion member.

2. The ultrasonic probe according to claim 1, wherein the light diffusion member includes plural light irradiating portions each configured to irradiate diffused light from the light source into the inspection subject.

3. The ultrasonic probe according to claim 2, wherein each of the plural light irradiating portions is positioned in front of a corresponding one of the receiving surfaces of the transducer array, in a direction of the ultrasonic wave from the inspection subject.

4. An ultrasonic probe comprising:
   a transducer array having a plurality of acoustic transducers each of which has a receiving surface so as to transduce an ultrasonic wave into an electrical signal;
   a light source;
   a light diffusion member connected to said light source so as to diffuse light emitted from said light source into an inspection subject,
   wherein said light diffusion member is laid over said transducer array so as to have a propagating surface through which the ultrasonic wave propagates in a direction through a thickness of said light diffusion member to said transducer array and a light irradiating surface in opposition to said propagating surface, and
   wherein said light diffusion member has said light irradiating surface located closer to the inspection subject than is said transducer array.

5. The ultrasonic probe according to claim 4, wherein said light diffusion member has a plurality of said light irradiating surfaces.

6. The ultrasonic probe according to claim 4, wherein each of the plurality of acoustic transducers is a capacitive micro-machined ultrasonic transducer.

7. The ultrasonic probe according to claim 6, wherein at least one of the plurality of said capacitive micro-machined ultrasonic transducers has a different receiving area from another of the plurality of said capacitive micro-machined ultrasonic transducers.

8. An inspection apparatus using the ultrasound probe according to claim 4, comprising:
   a signal processing unit configured to process an ultrasonic signal from said ultrasound probe;
   an image data processing unit configured to perform image reconstruction by using data from said signal processing unit; and
   a display unit configured to display information of the inspection subject obtained by said image data processing unit.

9. The inspection apparatus according to claim 8, further comprising:
   a light controlling unit configured to generate light pulses from said light source.

10. The ultrasonic probe according to claim 4, wherein said light diffusion member is configured to average a distribution of quantity of light irradiation.

11. The ultrasonic probe according to claim 4, wherein said light diffusion member is configured to provide light to the inspection subject while reducing a surface density of the light.

12. The ultrasonic probe according to claim 4, wherein said light diffusion member extends along an arrangement of said transducer array.

13. The ultrasonic probe according to claim 12, wherein said light diffusion member entirely covers said transducer array.

14. The ultrasonic probe according to claim 4, wherein said light diffusion member extends across a direction which an ultrasonic wave propagates from the inspection subject to said plurality of acoustic transducers.

15. The ultrasonic probe according to claim 4, wherein said light diffusion member has an acoustic transmittance property such as not to disturb said transducer array detecting the ultrasonic wave.

16. The ultrasonic probe according to claim 4, wherein said light diffusion member has a light guiding member connected to said light source and a scattering member connected to said light guiding member such that light emitted from said light source propagates through said light guiding member and is irradiated from said light irradiating surface.

17. The ultrasonic probe according to claim 4, wherein said light diffusion member extends along an extending direction from a first end to a second end, and wherein said light source is located next to one of said ends of said light diffusion member.

18. The ultrasonic probe according to claim 4, wherein the light diffusion member includes plural light irradiating portions each configured to irradiate diffused light from the light source into the inspection subject.

19. The ultrasonic probe according to claim 18, wherein each of the plural light irradiating portions is positioned in front of a corresponding one of the plural receiving surfaces of the transducer array, in a direction of the ultrasonic wave from the inspection subject.

20. The ultrasonic probe according to claim 4, wherein light emitted form said light source is diffused by the light diffusion member into the inspection subject without being disturbed by the transducer array.

21. The ultrasonic probe according to claim 4, wherein light emitted from said light source is diffused by the light diffusion member into the inspection subject in such a manner that distribution of light irradiation is averaged.

22. The ultrasonic probe according to claim 4, wherein light emitted from said light source is diffused by the light diffusion member into the inspection subject without passing the light through an area between transducer arrays.

23. The ultrasonic probe according to claim 4, wherein each said receiving surface is comprised of an acoustic receiving surface constructed to transduce an ultrasonic wave into an electrical signal, and
wherein the propagating surface is comprised of an acoustic propagating surface through which the ultrasonic wave propagates.

24. The ultrasonic probe according to claim 4, wherein said light diffusion member has said light irradiating surface located closer to the inspection subject than is said transducer array.

25. An ultrasonic probe comprising:
a transducer array having a plurality of acoustic transducers each of which has a receiving surface so as to transduce an ultrasonic wave from an inspection subject into an electrical signal such that the transducer array includes plural receiving surfaces;
a light source; and
a light diffusion member which diffuses light emitted from the light source into the inspection subject,
wherein the light diffusion member is laid over the transducer array and the plural receiving surfaces of the transducer array, and includes a propagating surface and a light irradiating surface in opposition to the propagating surface, wherein the light diffusion member is constructed so that the ultrasonic wave from the inspection subject propagates through the light diffusion member in a direction through a thickness of the light diffusion member to the receiving surfaces of the transducer array,
wherein the light diffusion member extends along an extending direction having a first optical end and a second optical end, and
wherein the light source is optically connected to the light diffusion member via at least one of the first optical end and the second optical end so as to diffuse light emitted from the light source into the inspection subject.

26. The ultrasonic probe according to claim 25, wherein the light diffusion member is positioned in front of the plural receiving surfaces of the transducer array.

27. The ultrasonic probe according to claim 25, wherein the light diffusion member includes plural light irradiating portions each configured to irradiate diffused light from the light source into the inspection subject.

28. The ultrasonic probe according to claim 27, wherein each of the plural light irradiating portions is positioned in front of a corresponding one of the plural receiving surfaces of the transducer array, in a direction of the ultrasonic wave from the inspection subject.

* * * * *